United States Patent
Buchanan et al.

(10) Patent No.: US 6,176,877 B1
(45) Date of Patent: *Jan. 23, 2001

(54) TWO PIECE PROSTHETIC HEART VALVE

(75) Inventors: Eric S. Buchanan, Wyoming; Bob Allan, Maple Grove; Michael J. Girard, Lino Lake, all of MN (US); William R. Holmberg, New Richmond, WI (US); Kimberly A. Anderson, Eagan, MN (US)

(73) Assignee: St. Jude Medical, Inc., St. Paul, MN (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/062,822

(22) Filed: Apr. 20, 1998

(51) Int. Cl.[7] ............................................ A61F 2/24
(52) U.S. Cl. ................................. 623/2.39; 623/2.4
(58) Field of Search ...................... 623/2, 900, 2.38, 623/2.39, 2.4, 2.41

(56) References Cited

U.S. PATENT DOCUMENTS

| | | |
|---|---|---|
| 3,143,742 | 8/1964 | Cromie . |
| 3,503,079 | 3/1970 | Smith . |
| 3,546,710 | 12/1970 | Shumakov et al. . |
| 3,574,865 | 4/1971 | Hamaker . |
| 3,587,115 | 6/1971 | Shiley . |
| 3,686,740 | 8/1972 | Shiley ................................... 29/439 |
| 3,996,623 | 12/1976 | Kaster . |
| 4,078,268 | 3/1978 | Possis . |
| 4,364,126 | 12/1982 | Rosen et al. . |
| 4,612,011 | 9/1986 | Kautzky ................................. 623/2 |
| 4,680,031 | 7/1987 | Alonso . |
| 4,705,516 | 11/1987 | Barone et al. ......................... 623/2 |
| 4,892,541 | 1/1990 | Alonso . |
| 5,032,128 | 7/1991 | Alonso . |
| 5,035,709 | 7/1991 | Wieting et al. ........................ 623/2 |
| 5,071,431 | 12/1991 | Sauter et al. ......................... 623/2 |
| 5,163,954 | 11/1992 | Curcio et al. ........................ 623/2 |
| 5,354,330 | 10/1994 | Hanson et al. ........................ 623/2 |
| 5,397,346 | 3/1995 | Walker et al. ......................... 623/2 |
| 5,562,729 | * 10/1996 | Purdy et al. .......................... 623/2 |
| 5,607,470 | 3/1997 | Milo .................................... 623/2 |
| 5,716,370 | 2/1998 | Williamson, IV et al. ........... 606/153 |
| 5,776,188 | 7/1998 | Shepherd et al. ..................... 623/2 |

FOREIGN PATENT DOCUMENTS

| | | |
|---|---|---|
| 1 180 087 | 10/1964 | (DE) . |
| 35 07 109 A1 | * 9/1986 | (DE) ..................................... 623/2 |
| 0 119 357 A1 | * 9/1984 | (EP) ..................................... 623/2 |
| 0 544 102 A1 | 6/1993 | (EP) . |
| 1 386 811 | 12/1964 | (FR) . |
| 1 600 506 | * 10/1981 | (GB) ..................................... 623/2 |
| 1 222 264 | 8/1983 | (SU) . |
| WO 87/05489 | 9/1987 | (WO) . |
| WO 91/14408 | 10/1991 | (WO) . |
| WO 96/03925 | 2/1996 | (WO) . |
| 96/12452 | * 5/1996 | (WO) ..................................... 623/2 |
| WO 97/09948 | 3/1997 | (WO) . |
| WO 97/30659 | 8/1997 | (WO) . |

* cited by examiner

*Primary Examiner*—David H. Willse
(74) *Attorney, Agent, or Firm*—Hallie A. Finucane, Esq.; Westman, Champlin & Kelly, P.A.

(57) ABSTRACT

A prosthetic heart valve for implantation in a heart includes an outer orifice ring for coupling to a tissue annulus of a heart. An inner orifice ring includes at least one leaflet occluder carried in a lumen of the inner orifice ring which is movable between an open position, which allows blood flow through the lumen, and a closed position which blocks blood flow through the lumen. The inner orifice ring is adapted to be coupled to the outer orifice ring after the outer orifice ring has been attached to the tissue annulus.

30 Claims, 5 Drawing Sheets

TWO PIECE PROSTHETIC HEART VALVE

FIELD OF THE INVENTION

The present invention relates to mechanical heart valve prostheses. More specifically, the invention relates to a mechanism for attaching and implanting heart valve prostheses.

BACKGROUND OF THE INVENTION

Implantable mechanical heart valves are used for replacement of defective valves in hearts of patients. One common method employs a sewing ring or suture cuff which is attached to and extends around the outer circumference of the mechanical valve orifice. The sewing cuff is made of a biocompatible fabric suitable for allowing a needle and suture to pass therethrough. The valves are typically sutured to a tissue annulus that is left when the surgeon removes the existing valve from the patient's heart. The sutures are tied snugly, thereby securing the valve to the heart.

Sewing cuffs are labor intensive and difficult to manufacture and are difficult to secure to the valve orifice. Further, attaching the suture cuff to the tissue annulus is time consuming and cumbersome. The complexity of suturing provides a greater opportunity for mistakes and requires a patient to be on cardiopulmonary bypass for a lengthy period. It is also desirable to provide a large lumen through the valve orifice relative to the overall valve diameter. However, techniques for attaching the sewing cuff to the valve orifice typically require the area of the valve lumen be reduced to accommodate an attachment mechanism. For example, the sewing cuff is typically retained between two rims of the valve orifice. One of the rims normally defines the outside diameter of the valve orifice and thus limits the size of the valve lumen.

Another technique for attaching heart valves uses a series of pins which pierce the tissue annulus of the heart. The pins are crimped or bent, thereby locking the valve to the heart tissue and preventing the valve from separating from the heart. This technique is described in U.S. Pat. Nos. 3,574,865 and 3,546,710. Another technique for attaching a prosthetic heart valve to the heart tissue is shown in U.S. Pat. No. 4,705,516 in which an outer orifice ring is sutured to the tissue annulus and an inner orifice ring is then screwed into the outer orifice ring. However, the rings are not locked together and may become unscrewed after extended use.

SUMMARY OF THE INVENTION

The present invention includes a prosthetic heart valve for implantation in a heart. The heart valve includes an outer orifice ring for coupling to a tissue annulus of a heart. An inner orifice ring includes an occluding mechanism such as at least one leaflet (occluder) carried in a lumen of the inner orifice ring which is movable between an open position, which allows blood flow through the lumen, and a closed position which blocks blood flow through the lumen. The inner orifice ring is adapted to be coupled to the outer orifice ring after the outer orifice ring has been attached to the tissue annulus.

In one aspect of the invention, the outer orifice ring is attached to the tissue annulus by a helical screw. In another aspect, the outer orifice ring is coupled to the inner orifice ring by a snap fit. Yet another aspect includes an attachment tool for coupling the inner orifice ring to the outer orifice ring.

DETAILED DESCRIPTION OF THE PREFERRED EMBODIMENTS

Figure 1:
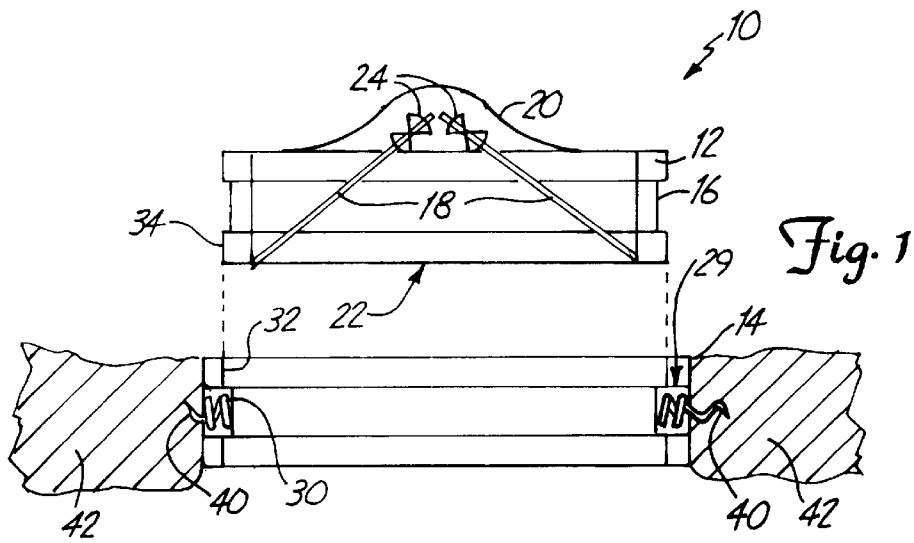
FIG. 1 is an exploded cross-sectional view of a prosthetic heart valve in accordance with the present invention.
Figure 2:
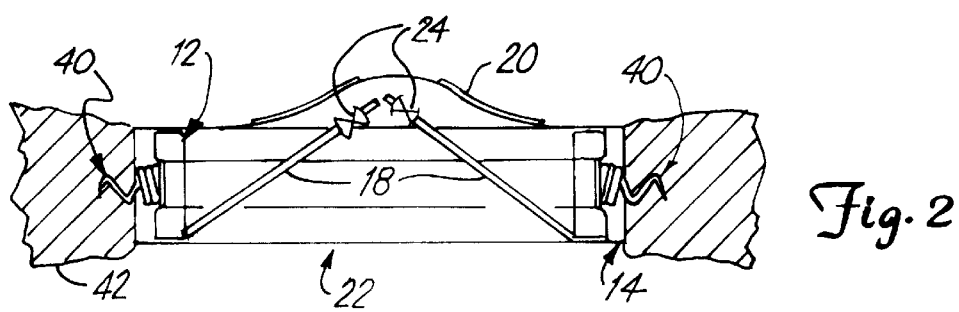
FIG. 2 is a cross-sectional view of the heart valve of FIG. 1.

The present invention includes a heart valve prosthesis 10 which is shown in FIG. 1 and includes an inner orifice ring 12 and an outer orifice ring 14. FIG. 1 is a side cross-sectional exploded view of valve 10 and FIG. 2 is an assembled cross-sectional view of valve 10.

Inner orifice ring 12 includes a locking recess 16 (or, in another embodiment, a ridge) formed around its outer circumference. Leaflets (or occluders) 18 provide an occluding mechanism and are pivotably coupled to ring 12 at a pivot guard 20. Leaflets or occluders 18 move between an open position (not shown) and a closed position as shown in FIGS. 1 and 2 in which flow of fluid through lumen 22 is blocked. Leaflets 18 rotate within pivots 24 formed in pivot guards 20. In one preferred embodiment, inner ring 12 comprises a prosthetic heart valve available from St. Jude Medical, Inc. of St. Paul, Minn., without a sewing cuff carried thereon. However, in some embodiments it may be preferable to use a specially designed inner ring 12.

Outer orifice ring 14 includes a locking ridge 30 (or, in another embodiment, a recess) formed on an inner annulus circumference thereon. The inner annulus 32 of ring 14 is sized to have approximately the same radius as outer annulus 34 of inner ring 12. Similarly, locking ridge 30 of outer ring 14 substantially conforms to locking recess 16 of inner ring 12. Locking recess 16 and locking ridge 30 cooperate to provide a ring coupling mechanism adapted to couple the outer orifice ring to the inner orifice ring. Outer orifice ring 14 also includes tissue annulus attachment locking mechanism 40 which, in one preferred embodiment, comprises helical screws carried through holes 29 around the other circumference of ring 14. Other types of attachment mechanisms include staples, pins, rivets, "nails", barbs, hooks, etc. These mechanisms could be coupled to or integral with the outer orifice ring. As illustrated in FIGS. 1 and 2, locking mechanism 40 attaches to the natural heart tissue annulus 42 of the patient.

Figure 3:
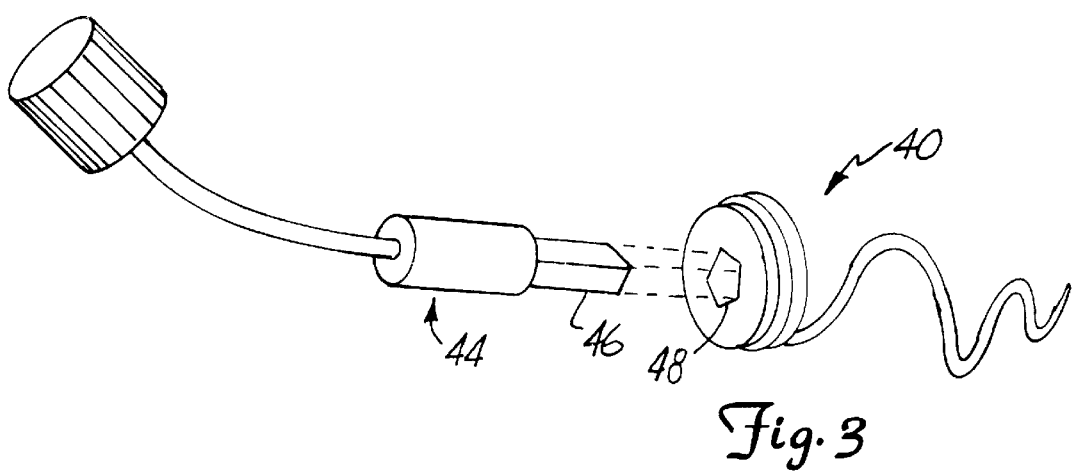
FIG. 3 is a perspective view of an attachment mechanism for the prosthetic heart valve of FIGS. 1 and 2.

FIG. 3 is a perspective view of locking mechanism 40 shown in greater detail. Locking mechanism 40 is a helical screw preferably made of a biocompatible material, such as a biocompatible metal. For example, locking mechanism 40 may be formed from a platinum-iridium alloy, MP35N (a cobalt-chrome-steel alloy) or titanium. As shown in FIG. 3, a tool 44 includes engaging tip 46 which fits into screw head 48. Locking mechanism 40 may be turned by rotating tool 44. In one preferred embodiment, there are between 8 and 12 substantially equally spaced locking mechanisms 40 around the circumference of inner orifice ring 12. However, any number may be used. Locking mechanism 40 typically extends between about 0.050 to about 0.100 inches into the tissue annulus 42.

Figure 4:
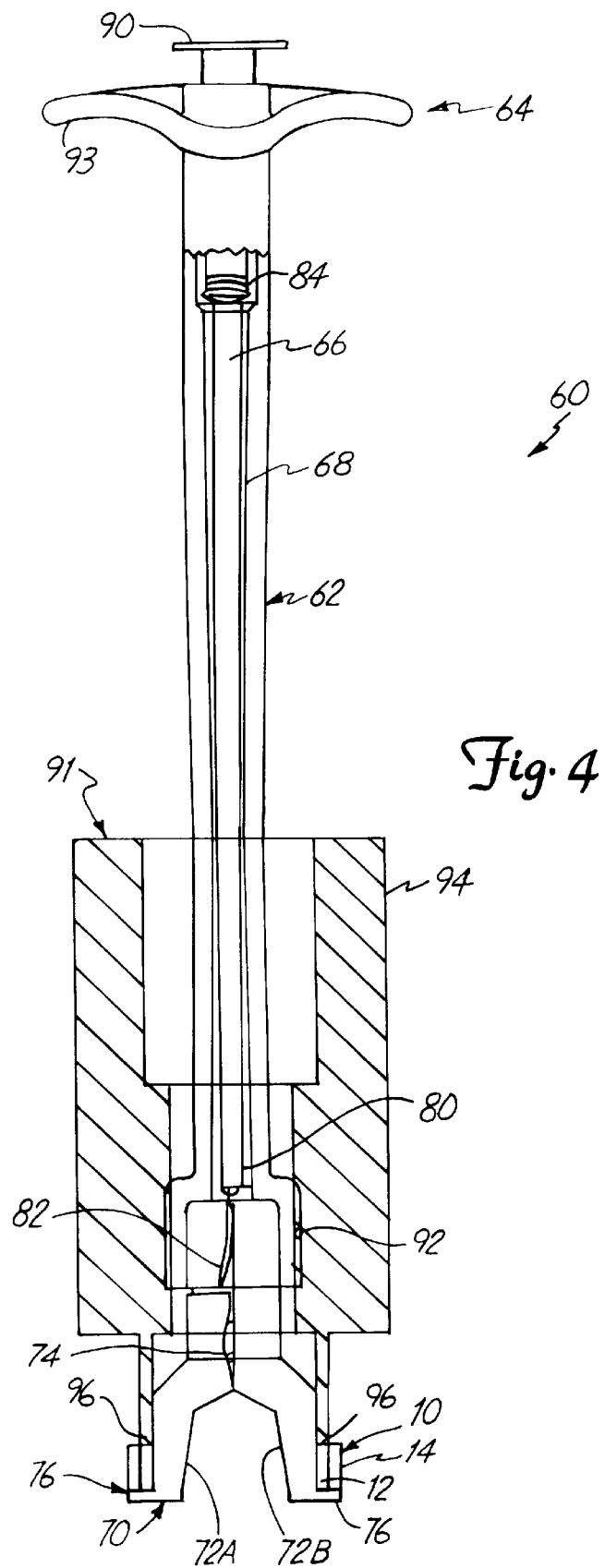
FIG. 4 is a side cross-sectional view of an implantation tool for implanting the heart valve prosthesis shown in FIGS. 1 and 2.

FIG. 4 is a side cross-sectional view of a tool 60 for use in implanting the heart valve prosthesis 10 shown in FIGS. 1 and 2. Tool 60 includes elongated handle 62 including a proximal gripping end 64. An actuator rod 66 extends through a center opening 68 in handle 62. A holder 70 is coupled to a distal end of handle 62. Holder 70 includes a moveable half 72A and a fixed half 72B coupled at pivot 74. Halves 72 include lower lip 76. A distal end 80 of actuator rod 66 couples to actuator cable 82 which is connected to half 72A. A spring 84 is coupled to actuator rod 66 and pushes actuator rod 66 in an axial direction away from holder 70 holding halves 72 in the closed position as shown in FIG. 4. Rod 66 includes actuator button 90. Proximal end 64 of handle 62 includes handle grip 93.

An orifice pushing mechanism 91 is aligned axially with handle 62 and coupled to handle 62 by threads 92. Mechanism 91 includes gripping portion 94 and orifice abutting surface 96. As shown in FIG. 4, orifice abutting surface 96 is adapted to abut inner orifice ring 12.

Figure 5:
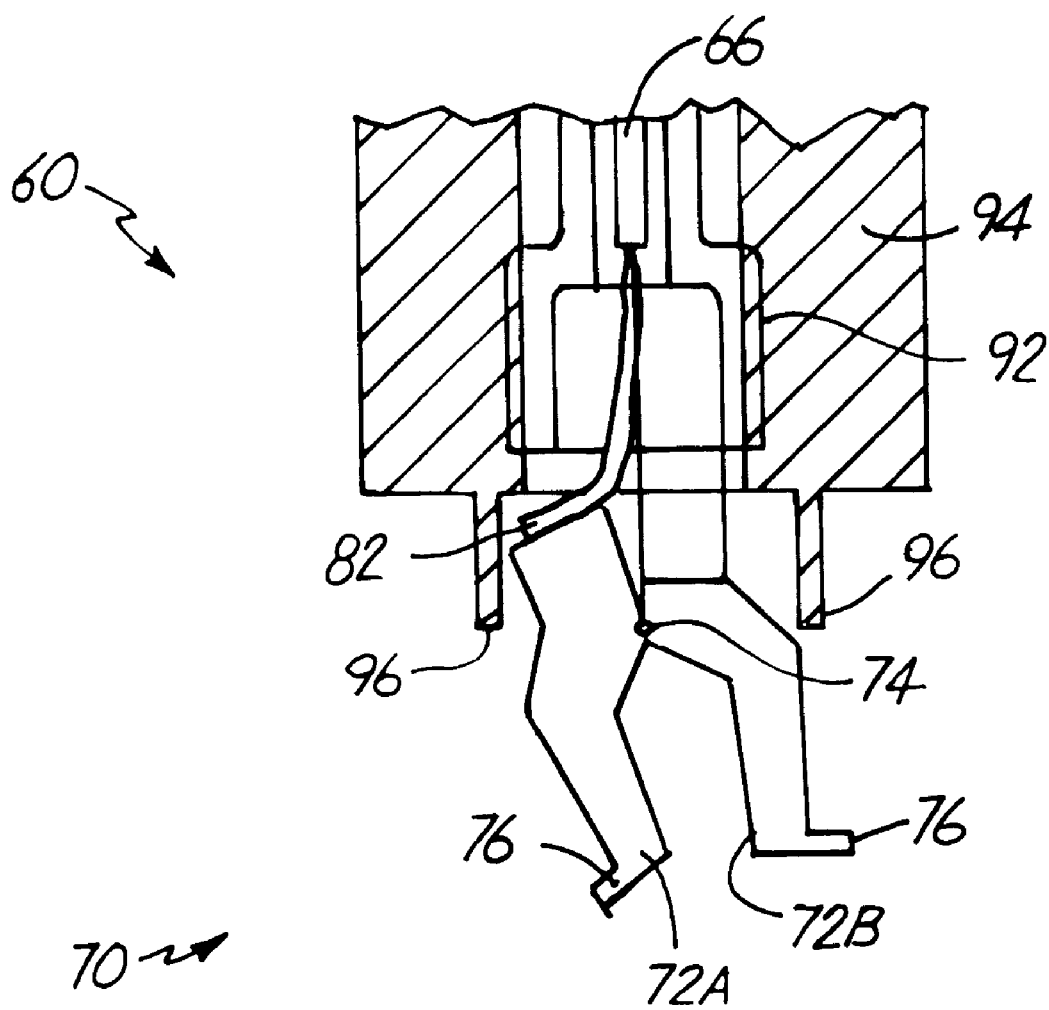
FIG. 5 is a side cross-sectional view of the tool of FIG. 4 in which a holder portion of the tool is moved to an open position.

FIG. 5 is a side cross-sectional view of a portion of tool 60 showing holder 70 in an open position in which half 72A is rotated about pivot 74. In this position, heart valve prosthesis 10 is freed from holder 70 such that heart valve prosthesis may be selectively removed from, or engaged with holder 70.

In operation, pressure is applied to actuation button 90 while grasping handle grip 93. This causes actuator rod 66 to move downward, towards the distal end of tool 60 whereby cable 82 causes half 72A to rotate about pivot 74. When pressure is released from actuator button 90, spring 84 pushes actuator rod 66 in a direction away from holder 70 such that half 72A is moved back into a closed position by cable 82 as shown in FIG. 4. After outer orifice ring 14 has been attached to the natural tissue annulus of the patient's heart, tool 60 containing pre-loaded ring 12 is inserted through implantable ring 14 by depressing actuator button 90. This engages lip 76 under ring 14. Mechanism 94 is then rotated whereby lip 76 and surface 96 work in opposing directions such that no axial force is applied to screws 40 or the patient's tissue annulus. Outer orifice ring is held against lower lip 76 such that a relative pressure is applied between rings 12 and 14. This causes locking ridge 30 to seat within locking recess 16. When the inner ring 12 has been "snapped" in place with ring 14, ring 12 prevents locking mechanisms 40 from unscrewing or disengaging. Force may then be applied to actuator button 90 such that half 72A of holder 70 rotates as shown in FIG. 5 so that tool 60 may be removed from prosthesis 10.

Figure 6:
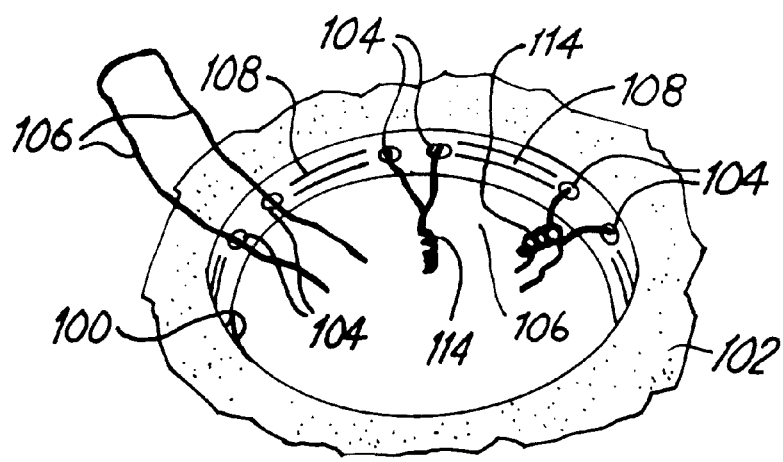
FIG. 6 is a side perspective view of an outer orifice ring in accordance with another embodiment.
Figure 7A:
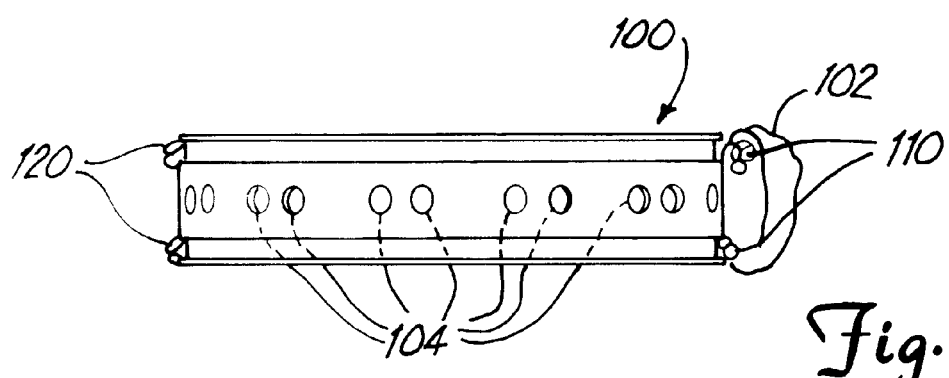
FIG. 7A is a side plan view and FIG. 7B is a side cross-sectional view of the outer orifice ring shown in FIG. 6.
Figure 7B:
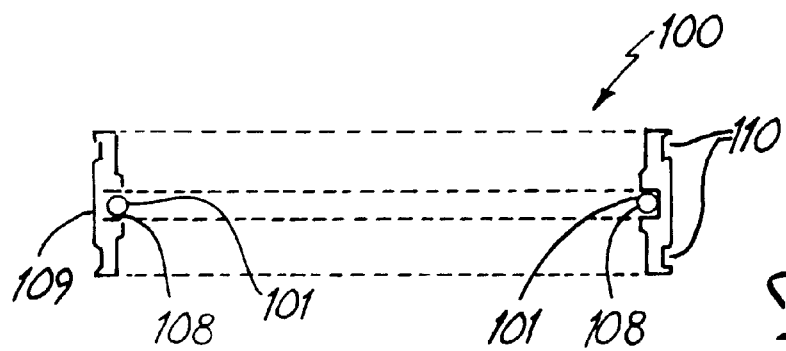

FIG. 6 is a perspective view of an outer orifice ring 100 in accordance with another embodiment which is coupled to a suture cuff 102. In the embodiment of FIG. 6, ring 100 includes a plurality of suture holes 104 formed therein for receiving sutures 106. Further, the inner annulus of ring 100 includes suture receiving groove 108. FIG. 7A is a side plan view of outer ring 100 and FIG. 7B is a side cross-sectional view of outer ring 100. As shown in FIG. 7A, the outer annulus of ring 100 includes cuff retaining grooves 110 formed therein. In one preferred embodiment, O-rings 101 are provided to prevent leakage between the orifice rings. Retaining sutures are wound circumferentially through cuff 102 and within cuff retaining grooves 110 binding or clamping cuff 102 to ring 100.

Ring 100 is sutured to tissue annulus 42 shown in FIG. 1 using sutures 106 which extend through cuff 102 and suture holes 104. Preferably, sutures 106 are metal sutures of a biocompatible material such as stainless steel. After the sutures 106 are threaded through the patient's natural tissue annulus and outer orifice ring 100, the surgeon secures the suture using knots 114 which may be formed by twisting the suture 106 as shown in FIG. 6. Excess suture material is then trimmed and knots 114 are folded into suture grooves 108.

Figure 8:
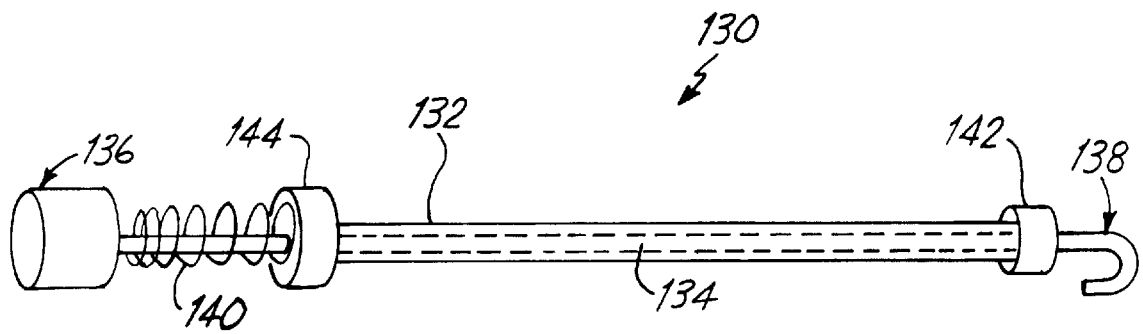
FIG. 8 is a side perspective view of a suture securing tool of the present invention.

FIG. 8 is a side perspective view of a suture securing tool 130 for use in twisting sutures 106 shown in FIG. 6. Tool 130 includes elongated body 132 carrying a shaft 134 therethrough between an actuator 136 and a hook 138. A spring 140 pushes on shaft 134 and body 132 such that hook 138 presses against end cap 142. By pressing on actuator 136, hook 138 may be extended to hook both ends of a suture 106. When actuator 136 is released, the suture 106 is trapped between hook 138 and cap 142. Tool 130 is then rotated to twist sutures 106 together forming twisted knots 114 shown in FIG. 6.

Following implantation of ring 100 into the tissue annulus 42, an inner orifice ring 12 as shown in FIG. 1 is coupled to ring 100 as described with respect to FIGS. 1–5.

Figure 9:
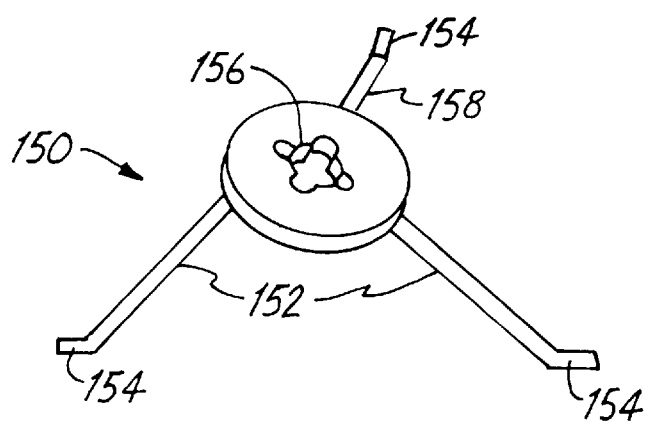
FIG. 9 is a perspective view of a holder for use in implanting an outer ring of a heart valve in accordance with the invention.

FIG. 9 is a perspective view of an implantation tool 150 for use in implanting orifice ring 100. Tool 150 includes legs 152 having coupling tips 154 which are configured to couple to ring 100. Tool 150 may be used by the surgeon to hold ring 100 during suturing such that force may be applied to ring 100. Tips 154 may be fit into suturing grooves 108. Tool 150 includes handle attachment opening 156 which may be used to selectively engage an elongated handle (not shown).

Preferably, the rings set forth herein are formed of biocompatible materials such as ultrahigh molecular weight polyethylene (preferably flexible and compliant) for the outer ring and titanium, MP35N, ceramic, pyroltic carbon or other rigid polymers for the inner ring. In general, the present invention is not limited to the particular embodiments set forth herein. For example, the particular shapes of the orifice rings and attachment mechanisms may be modified as appropriate and such modifications are considered to be within the scope of the invention. The ring coupling mechanism for coupling the two rings may be any mechanism as desired and is not limited to the particular "snap" coupling techniques set forth herein. For example, the coupling techniques may include screws, wires, bayonet locking mechanism, and nails which extend axially and engage the rings. Further, the configuration of the inner orifice ring and its occluding mechanism may be other than those set forth herein.

The present invention provides various advantages including a reduction in implantation time and relatively simple implantation technique. Further, the angular positioning of the leaflets in the inner ring is easily accomplished by rotating the inner ring with respect to the outer ring. The invention allows surgical access to subvalvular features prior to coupling the inner ring to the outer ring without the possibility of damaging the occluding mechanism, for example. The inner valve ring can be removed and replaced without excising the entire prosthesis. The invention reduces the complexity of surgery because manual suturing may not be required. The invention also allows an increase in the area of the lumen over typical prior art designs and a lower profile because the cuff attachment mechanism requires less area. With the inner ring coupled to the outer ring, the outer ring attachment mechanisms are completely shielded from blood flow where they could otherwise initiate formation of thrombus.

Although the present invention has been described with reference to preferred embodiments, workers skilled in the art will recognize that changes may be made in form and detail without departing from the spirit and scope of the invention. For example, any type of occluding mechanism may be used and the attachment mechanism may be integral with the ring body.

What is claimed is:

1. A prosthetic heart valve for implantation in a heart, comprising:
   an outer orifice ring;
   an attachment mechanism comprising at least one helical screw on the outer orifice ring adapted to couple the outer orifice ring to a tissue annulus of the heart;
   an inner orifice ring having an occluding mechanism carried therein; and
   a ring coupling mechanism adapted to couple the outer orifice ring to the inner orifice ring after the outer orifice ring has been coupled to the tissue annulus.

2. The prosthetic heart valve of claim 1 including a plurality of helical screws substantially evenly placed around a circumference of the outer orifice ring.

3. The prosthetic heart valve of claim 1 wherein the ring coupling mechanism comprises a locking ridge formed on a circumference of one of the rings and a locking recess formed on a circumference of the other of the rings, wherein the locking ridge snap fits in the locking recess to thereby secure the two rings together.

4. The prosthetic heart valve of claim 3 wherein the locking ridge extends around an inner circumference of the outer orifice ring and the locking recess extends around an outer circumference of the inner orifice ring.

5. The prosthetic heart valve of claim 1 wherein the occluding mechanism comprises a pair of moveable leaflets pivotably carried in a lumen through the inner orifice ring, the leaflets being moveable between an open position allowing blood flow therethrough and a closed position blocking blood flow therethrough.

6. The prosthetic heart valve of claim 1 wherein the at least one helical screw comprises a cobalt-nickel-chromium-molybdenum alloy.

7. The prosthetic heart valve of claim 1 wherein the inner orifice ring secures the attachment mechanism and shields the outer orifice ring and the attachment mechanism from blood flow when the inner orifice ring is coupled to the outer orifice ring.

8. The prosthetic heart valve of claim 1 wherein the ring coupling mechanism allows limited rotational movement about an axis of the inner orifice ring relative to an axis of the outer orifice ring.

9. The prosthetic heart valve of claim 1 including a seal between the outer orifice ring and the inner orifice ring to provide a fluidic seal therebetween.

10. A prosthetic heart valve for implantation in a heart, comprising:
    an outer orifice ring including a plurality of preformed holes formed therein and arranged around the ring to define suture locations, the holes extending in a direction which is generally perpendicular to an axis of the outer orifice ring;
    an attachment mechanism comprising a suture on the outer orifice ring, the suture shaped to extend through the holes in the outer orifice ring and couple the outer orifice ring to a tissue annulus of the heart;
    an inner orifice ring having an occluding mechanism carried therein; and
    a ring coupling mechanism configured to couple the outer orifice ring to the inner orifice ring after the outer orifice ring has been coupled to the tissue annulus.

11. The prosthetic heart valve of claim 10 wherein the ring coupling mechanism comprises a locking ridge formed on a circumference of one of the rings and a locking recess formed on a circumference of the other of the rings, wherein the locking ridge snap fits in the locking recess to thereby secure the two rings together.

12. The prosthetic heart valve of claim 11 wherein the locking ridge extends around an inner circumference of the outer orifice ring and the locking recess extends around an outer circumference of the inner orifice ring.

13. The prosthetic heart valve of claim 10 wherein the occluding mechanism comprises a pair of moveable leaflets pivotably carried in a lumen through the inner orifice ring, the leaflets being moveable between an open position allowing blood flow therethrough and a closed position blocking blood flow therethrough.

14. The prosthetic heart valve of claim 10 wherein the inner orifice ring shields the outer orifice ring attachment mechanism from blood flow when the inner orifice ring is coupled to the outer orifice ring.

15. The prosthetic heart valve of claim 10 wherein the ring coupling mechanism allows limited rotational movement about an axis of the inner orifice ring relative to an axis of the outer orifice ring.

16. The prosthetic heart valve of claim 10 wherein the outer orifice ring includes a recess formed on an inner annulus, the recess adapted to cover the suture.

17. The prosthetic heart valve of claim 10 including a suture cuff carried on an outer annulus of the outer orifice ring and wherein the suture is adapted to extend through the suture cuff.

18. The prosthetic heart valve of claim 10 including a seal between the outer orifice ring and the inner orifice ring to provide a fluidic seal therebetween.

19. A prosthetic heart valve for implantation in a heart, comprising:
    an outer orifice ring including a plurality of preformed holes arranged around the ring to define suture or screw locations;
    an attachment mechanism on the outer orifice ring adapted to couple the outer orifice ring to a tissue annulus of the heart;
    an inner orifice ring having an occluding mechanism carried therein;
    a ring coupling mechanism configured to couple the outer orifice ring to the inner orifice ring after the outer orifice ring has been coupled to the tissue annulus; and
    wherein the ring coupling mechanism comprises a locking ridge formed on a circumference of one of the rings and a locking recess formed on a circumference of the other of the rings, wherein the locking ridge snap fits in the locking recess to thereby secure the two rings together, the locking recess configured to cover the attachment mechanism.

20. The prosthetic heart valve of claim 19 wherein the attachment mechanism comprises at least one helical screw.

21. The prosthetic heart valve of claim 20 including a plurality of helical screws substantially evenly placed around a circumference of the outer orifice ring.

22. The prosthetic heart valve of claim 20 wherein the at least one helical screw comprises platinum-iridium.

23. The prosthetic heart valve of claim 19 wherein the locking ridge extends around an inner circumference of the outer orifice ring and the locking recess extends around an outer circumference of the inner orifice ring.

24. The prosthetic heart valve of claim 19 wherein the occluding mechanism comprises a pair of moveable leaflets pivotably carried in a lumen through the inner orifice ring, the leaflets being moveable between an open position allowing blood flow therethrough and a closed position blocking blood flow therethrough.

25. The prosthetic heart valve of claim 19 wherein the inner orifice ring secures the attachment mechanism and shields the outer orifice ring attachment mechanism from blood flow when the inner orifice ring is coupled to the outer orifice ring.

26. The prosthetic heart valve of claim 19 wherein the ring coupling mechanism allows limited rotational movement about an axis of the inner orifice ring relative to an axis of the outer orifice ring.

27. The prosthetic heart valve of claim 19 wherein the attachment mechanism comprises a suture.

28. The prosthetic heart valve of claim 27 including a suture cuff carried on an outer annulus of the outer orifice ring and wherein the suture is adapted to extend through the suture cuff.

29. The prosthetic heart valve of claim 27 wherein the outer orifice ring includes a recess formed on an inner annulus, the recess adapted to receive the suture.

30. The prosthetic heart valve of claim 27 including a seal between the outer orifice and the inner orifice ring to provide a fluidic seal therebetween.

* * * * *